United States Patent [19]

Brewer et al.

[11] Patent Number: 4,696,907

[45] Date of Patent: * Sep. 29, 1987

[54] IDENTIFICATION OF REAGINS IN THE BLOOD SERUM OF ALLERGEN SENSITIZED VERTEBRATES

[75] Inventors: John H. Brewer; Terry L. Foster, both of Abilene, Tex.

[73] Assignee: Science Research Center, Inc., Abilene, Tex.

[*] Notice: The portion of the term of this patent subsequent to May 10, 2000 has been disclaimed.

[21] Appl. No.: 645,665

[22] Filed: Aug. 30, 1984

Related U.S. Application Data

[60] Division of Ser. No. 493,413, May 10, 1983, Pat. No. 4,486,540, which is a continuation-in-part of Ser. No. 323,762, Nov. 23, 1981, abandoned, which is a division of Ser. No. 170,143, Jul. 18, 1980, Pat. No. 4,331,650.

[51] Int. Cl.$^4$ .................. G01N 33/539; G01N 33/547
[52] U.S. Cl. .................................. 436/513; 436/524; 436/527; 436/528; 436/531; 436/532; 436/533; 436/534
[58] Field of Search .............. 436/513, 524, 527, 528, 436/531, 532, 533, 534

[56] References Cited

U.S. PATENT DOCUMENTS

| | | | |
|---|---|---|---|
| 3,564,089 | 2/1971 | Kiddy | 436/534 |
| 3,720,760 | 3/1973 | Bennich et al. | 436/513 X |
| 4,060,597 | 11/1977 | Sato | 436/534 |
| 4,164,558 | 8/1979 | von Schulthess et al. | 436/531 |
| 4,184,849 | 1/1980 | Cambiaso et al. | 436/533 X |
| 4,203,724 | 5/1980 | Sawai et al. | 436/533 X |
| 4,218,335 | 8/1980 | Mochida et al. | 435/188 X |
| 4,232,119 | 11/1980 | Carlsson et al. | 435/7 |
| 4,256,833 | 3/1981 | Ali et al. | 435/7 |
| 4,273,756 | 6/1981 | Ling et al. | 436/513 X |
| 4,276,259 | 6/1981 | Eibl et al. | 436/542 X |
| 4,279,617 | 7/1981 | Masson, II | 436/538 |
| 4,486,540 | 12/1984 | Brewer | 436/534 |
| 4,590,170 | 5/1986 | Ariyoshi | 436/528 |
| 4,598,051 | 7/1986 | Papahadjopoulos | 436/533 |

FOREIGN PATENT DOCUMENTS

| | | | |
|---|---|---|---|
| 1248765 | 10/1971 | United Kingdom | 436/513 |
| 1362776 | 8/1974 | United Kingdom | 436/533 |

Primary Examiner—Sam Rosen
Assistant Examiner—Robert Benson
Attorney, Agent, or Firm—Kane, Dalsimer, Kane, Sullivan and Kurucz

[57] ABSTRACT

The disclosure is a method for the in-vitro detection and identification of reagins in the blood serum of allergen sensitized vertebrates. The method comprises admixing the blood serum of the vertebrate with solid, porous carrier particles bearing surface adsorbed, known allergens. An agglutination reaction indicates the presence of reagins corresponding to the surface adsorbed allergen.

8 Claims, 1 Drawing Figure

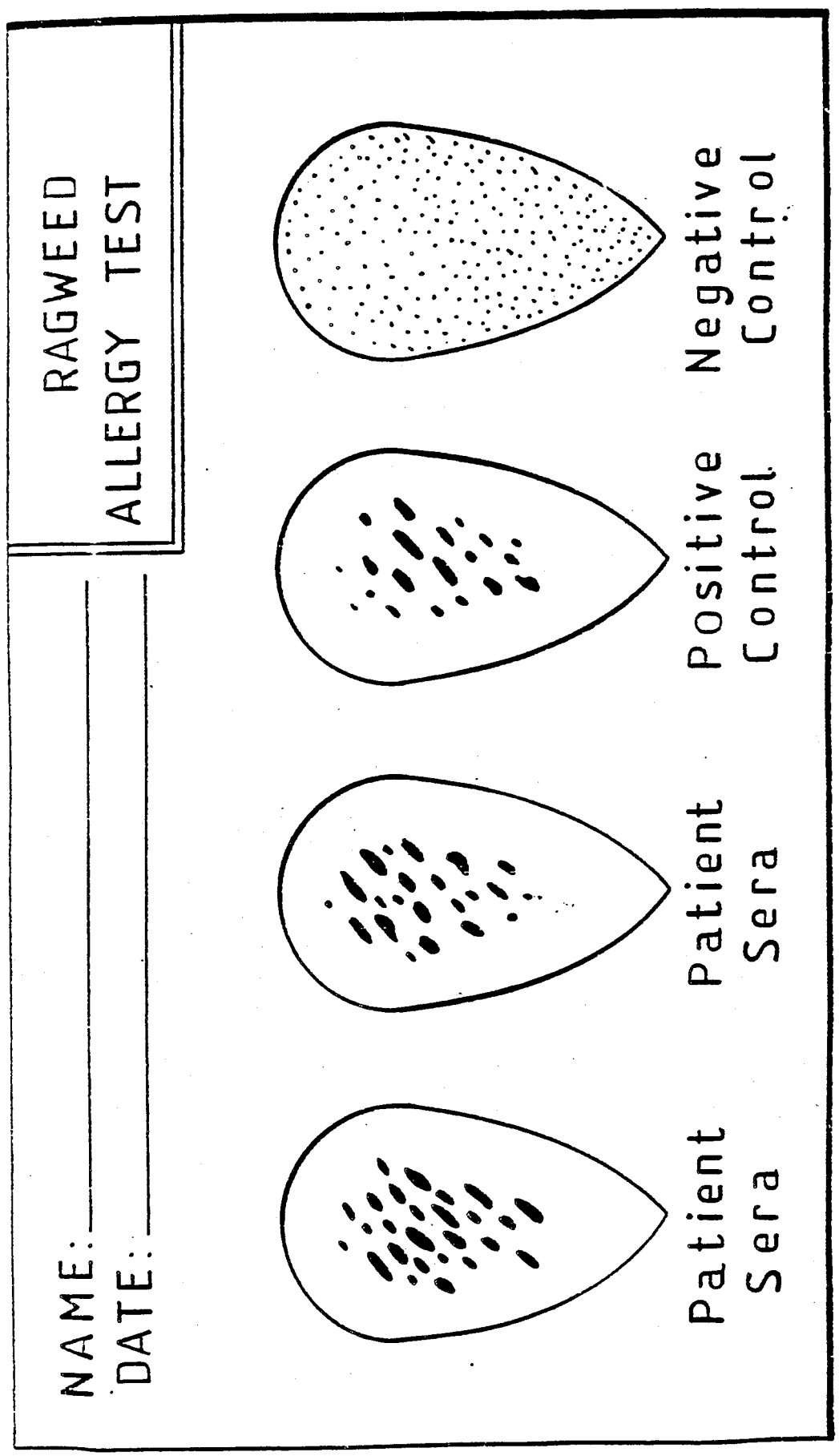

IDENTIFICATION OF REAGINS IN THE BLOOD SERUM OF ALLERGEN SENSITIZED VERTEBRATES

CROSS-REFERENCE TO RELATED APPLICATIONS

This application is a division of U.S. patent application Ser. No. 493,413, filed May 10, 1983, now issued as U.S. Pat. No. 4,486,540, and which was a continuation-in-part of application Ser. No. 323,762 filed Nov. 23, 1981, now abandoned, which was a division of application Ser. No. 170,143 filed Jul. 18, 1980 and now issued as U.S. Pat. No. 4,331,650.

BACKGROUND OF THE INVENTION

1. Field of the Invention

The invention relates to an in-vitro method of identifying reagins present in the blood serum of allergen sensitized vertebrates, including humans.

2. Brief Description of the Prior Art

Reagins are complex organic compounds belonging to the class of immunoglobulins known as immunoglobulin E (generally referred to for convenience as "IgE"). More specifically reagins are a group of type IgE proteins found in the blood serum of vertebrates, following their sensitization by exposure to an allergen or allergens. Sensitization comprises the endogeneous production of the reagin by the vertebrate, stimulated by the presence of the allergen. The mechanism for reagin production is a matter for speculation. The endogeneously produced reagin may be characterized in part by its antibody-like activity, i.e., its specific reactivity in binding at epitopic sites on the counterpart allergen which is the source of its own genesis. The reagin also generally has a propensity to attach to living cells throughout the body of the host vertebrate. When the counterpart allergen is reintroduced into the previously sensitized host vertebrate, an allergen-reagin reaction takes place usually with a consequential anaphylactoid type of immune reaction. The latter results primarily from a rupture of eosinophils and basophils having attached reagins - allergen complex. Rupture of the cells releases histamine, slow-reacting substance of anaphylaxis, eosinophil chemotaxic substance, lysosomal enzymes and other compounds which result in an allergic reaction in the host vertebrate. Allergic reactions include anaphylaxis, urticaria, hay-fever, asthma and like clinical manifestations.

To avoid allergen-reagin reactions in a sensitized vertebrate, one hopefully identifies reagins in the blood serum of the vertebrate and then precautions may be taken to limit exposure of the sensitized individual to allergens corresponding to the identified reagin or reagins or by desensitizing the individual to specific allergens.

In view of reagin antibody activity, prior art in-vitro methods of identifying reagins in blood serum have been based, empirically, on the known and classic immunological relationship which exists between an antigen and its corresponding antibody. However, such prior art methods have not been entirely satisfactory in regard to reagin identification for a number of reasons. First, allergens, which are in essence protein substances foreign to the chemistry of a given vertebrate, apparently stimulate the production of relatively small quantities of reagin in comparison for example to the production of antibody to disease antigens. The smaller production of reagin complicates its detection and identification in the complex mixture comprising blood serum.

Additionally, the majority of native allergens possess a plurality of allergenic determinants and when introduced into a vertebrate will provoke or elicit a mixed plurality of reagins instead of a single reagin. The mixture of reagins will differ from each other in their physicochemical and biological properties, complicating further identification of the reagin entity. Some of the minor reagin compounds elicited in the mixture may be in such low concentrations that they are not detectable by conventional physicochemical techniques.

Secondly, since most IgE material isolated from host organisms has been found to be a heterogeneous mixture of structurally similar but diverse proteins, and a specific reagin may in fact be a mixture of different reagin molecules, any in-vitro detection method based on binding of the reagin with an allergen may depend for accuracy on a protocol which may or may not account for all of the diverse reagin molecules and not just a portion of the mixture.

In addition, it will be appreciated that since immune sera contains reagins which will bind to their corresponding allergens with varying degrees of avidity, strong positive allergen-reagin reactions may not always be obtained in reasonable times. Further, the physical nature of the reagin mixture might be expected to affect the strength of any interaction or binding of reagin which may occur.

It has also been recognized that IgE materials do not behave in the same way as, for example, IgM or IgG the protective antibodies produced by an organism to counteract antigens related to diseases. In the latter process, the host organism may continue to produce "protective" types of antibody even after the disease state or entity has been eliminated, thereby obtaining immunity to re-infection. In contrast, in the case of allergy whose physical manifestation of the allergic response is the binding of the allergen with the reagin, no immunity is necessarily conferred. When the binding reaction occurs, cellular damage occurs wherein substances such as histamine are released to affect allergic target tissues. The binding reaction will occur during every subsequent re-introduction of allergen into the host organism.

Clearly, although there are apparant analogies between the classical immunological antigen-antibody relationship and the more specific allergen-reagin process, there are also subtle and marked differences. It is these differences which suggest that the prior art empirical use of antigen-antibody in-vitro identification procedures to identify allergens-reagins may have been misplaced and accounts for the inaccuracies which have been observed (lack of avidity, specificity) and the lack of sensitivity.

Because of the dissatisfactions with the prior art in-vitro methods of determining and identifying reagins in blood serums, the most widely employed methods of determining reagins present in the blood serum of allergen sensitized vertebrates (and thereby a differential diagnosis of atopic or anaphylactic allergy) are the in-vivo skin and provocation test methods. These in-vivo test methods are also lacking in complete satisfaction. They are time consuming, inconvenient to patients and not without serious risk. The potential for anaphylaxis upon exposure of the patient to allergens is a real hazard.

Like the prior art in-vitro methods for identifying reagins, the in-vivo methods are also inaccurate to a degree. The allergen-reagin reaction physical manifestations observed in skin-testing may be affected by subjective influences such as an allergic threshold in individual body resistance to allergic response. Emotional factors in the individual undergoing testing can also affect the allergic response.

In summary the prior art methods, both in-vitro and in-vivo, for identifying reagins in the blood sera of vertebrates have not been entirely reliable, accurate or safe for the variety of reasons described above. The method of the present invention is an improvement over in-vitro testing, based on the adsorption of an allergen on a water-insoluble carrier particle and agglutination of the particles in the presence of the reagin counterpart of the adsorbed allergen.

There are a number of advantages associated with the method of our invention. A major advantage resides in the capability of performing allergen identification testing in the physician's office on a simple, economical and rapid basis. The use of the patient's blood serum in an in-vitro test method obviates the hazards associated with conventional skin-testing and provocation test proecedures (risk of anaphylaxis). This is particularly advantageous where the very young, elderly and debilitated individual is the object of testing. Other advantages include more stable reagents with less associated hazards and which require less training in their use than those associated with, for example, the radioallergoimmunosorbent test (RAST) which employs radioactive labelled reagents. The reagents used in the method of the invention also have longer shelf-lives than radioactive labelled reagents and are safer to use.

The method of the invention also requires only small blood serum samples for testing (less than 5.0 ml), providing the patient with considerably decreased discomfort and loss of time. Once the blood sample is obtained the patient need not wait for results. Automation of the procedure will enable the physician to increase the number of patents he can diagnose in a given time period.

Because the method of the invention measures specific IgE it enables the physician to monitor allergy therapy by monitoring serum IgE levels. This is a very sensitive monitor. In contra-distinction skin test results fluctuate rapidly over short periods of time depending on the physical state of the patient. The method of the invention is more consistent and repeatable than skin-testing because it comprises monitoring serum components which are less affected by the patient's physical condition.

SUMMARY OF THE INVENTION

The invention comprises a method of determining the presence or absence of a given reagin in the blood serum of a vertebrate sensitized by the allergen counterpart of said reagin, which comprises;

A. providing an extra-corporeal specimen of the blood serum suspected of containing the reagin;
B. providing an aqueous dispersion of solid, porous carrier particles having adsorbed thereon an allergen corresponding to said allergen counterpart;
C. admixing the blood specimen provided with the aqueous dispersion; and
D. observing the admixture for an agglutination reaction;

wherein a positive agglutination reaction is indicative of the presence of the reagin and the absence of an agglutination reaction is indicative of the absence of the reagin.

The identification of reagins in the blood serum of sensitized vertebrates, including humans is useful for the diagnosis of atopic allergies and thus subsequent treatment and/or avoidance of allergen associated substances which may be harmful to the sensitized individual.

BRIEF DESCRIPTION OF THE DRAWING

The FIGURE is a plan view of a test card showing the results of a reagin identification test carried out according to the method of the invention.

DETAILED DESCRIPTION OF THE INVENTION

An initial step in the method of the invention is the provision of an aqueous dispersion of finely divided, solid porous, carrier particles having adsorbed thereon a given and known allergen corresponding to the allergen counterpart of the reagin to be determined (presence identified). Solid carrier particles employed are represented by finely divided particles of silica, ion-exchange resins, alumina, kaolin, bentonite, graphite, charcoal, quartz, protein particles, organic polymeric resins, latex particles and like water-insoluble material. Preferred are non-polar materials such as carbon black, charcoals, graphite, organic resins, paraffin, synthetic organic polymers, talc and the like since these non-polar materials form excellent homogeneous dispersions in water. The particles are advantageously within an average size range of from 0.5 to 15 $\mu$m, preferably 0.5 to 2.0 $\mu$m in diameter and the aqueous dispersions prepared therefrom advantageously contain a concentration of the solid particles within the range of from about 0.005 to 0.5 percent by weight, preferably about 0.02 percent.

The solid carrier particles have adsorbed on their surfaces, a given and known allergen. The technique of adsorption comprises an admixture of the insoluble solid carrier material. The soluble allergen is surface adsorbed on the carrier particles over a period of time under specific conditions. The degree of adsorption and the time required for adsorption will vary depending on the physical nature of the carrier particles, but may be determined by a conventional technique such as by a trial and error technique.

Allergens are generally polar molecules and as such are only poorly adsorbed from a solute by non-polar surfaces such as surfaces of carbon black, charcoals, graphite, organic resins, synthetic polymers, paraffin, stibnite, talc and the like. Treatment of the non-polar surface to render it more hydrophilic is not desirable, because such would lower the dispersion forces which advantageously provide a homogeneous dispersion of the particles in an aqueous system.

We therefore preferably enhance adsorption of the allergen on the preferred non-polar surfaces by conversion of the allergen to a complex containing both polar and non-polar groups, possessing characteristics of a surfactant. These complexes, having surfactant properties to promote their adsorption on the non-polar particle surfaces also surprisingly retain the biochemical activity of the allergen moiety of the complex. The complex is resistant to desorption from the surface of the carrier particle once adsorbed thereon. Resistance to desorption ultimately results in amplification of the agglutination reaction which may occur when the carrier particles with adsorbed allergen are exposed to reagins, as hereinafter described more fully.

The term "surfactant" as used herein is a contraction of "surface-active agent" and is a broadly descriptive term used to describe a chemical compound which is (1) soluble in at least one phase of a system, (2) has an amphipathic structure, (3) the molecules of which form oriented monolayers at phase interfaces, (4) exhibits an equilibrium concentration as a solute at a phase interface, greater than its concentration in the bulk of the solution, (5) forms micelles when the concentration as a solute in solution, exceeds a characteristic limiting value and (6) exhibits some combination of the functional properties of detergency, foaming, wetting, emulsifying, solubilizing and dispersing. In view of the surfactant character of the allergen complexes formed and used in the method of the invention, it is surprising that they actually enhance or amplify the agglutination reaction described more fully hereinafter.

The surfactant allergen complex adsorbed on carrier particles and used in the present invention may be prepared by bringing together the allergen with a compound of the general formula:

$$X-Y \qquad (I)$$

wherein X represents a hydrophilic, polar moiety and Y represents a hydrophobic, non-polar moiety. The compound of formula (I) will complex with the allergen according to the reaction scheme:

$$\text{\textcircled{A}} + X-Y \longrightarrow \text{\textcircled{A}} \; X-Y$$
$$(I) \qquad\qquad (II)$$

wherein X and Y are as previously defined and A represents the polar allergen molecule. It will be observed from the above reaction scheme that the product complex (II) of allergen/compound (I) is one wherein the hydrophilic or polar moiety X of the compound (I) is turned or oriented toward the polar allergen molecule and the hydrophobic, non-polar Y moiety is oriented away from the polar allergen molecule. When the allergen/compound (I) complex is mixed in a solute with the solid, non-polar carrier particles, the non-polar Y moiety orients toward the non-polar surface of the carrier particle. This, of course is ideal for adsorption of the allergen/compound (I) complex from the aqueous mixture since the polar portion X orients toward the aqueous phase (polar phase) and the non-polar portion Y is most readily adsorbed by the non-polar surface of the carrier particle.

Allergen materials are readily available, usually as extracts of naturally occurring substances. Preferably the allergens employed to form the complexes of Formula (II) described above are relatively pure and free of contaminants. The allergens are advantageously mixed with the compound (I) in a proportion of from about 1.0 to 50.0 mg/ml. of allergen to 0.1 to about 1.0 mg/ml. of the compound of formula (I). Following admixture, the resulting mixture may be incubated for from 15 to 60 minutes at room temperatures to allow the desired complex (II) to form.

Representative of compounds of the formula (I) are those in which the polar group X is selected from phosphato, carboxylic, sulphato, amino, hydroxyl, choline and like groups and the non-polar group Y is selected from a saturated or unsaturated aliphatic hydrocarbon group (such as alkyl or alkylene), an aliphatic hydrocarbon group substituted by at least one aromatic or cycloaliphatic group and the like. Preferably, the compound of formula (I) is a phospholipid such as lecithin, phosphatidylethanolamine, lysolecithin, lysophosphatedylethanolamine, phosphatidylserine, phosphatidylinositol, sphingomyelin, cardiolipin, phosphatidic acid, the cerebrosides and the like. In a most preferred embodiment of the process, a mixture of compounds of the formula (I) are employed, at least one of which is a phospholipid as described above and the other or others are non-phospholipids such as stearylamine, dicetyl phosphate, cholesterol, tocopherol and the like.

The surfactant complex of allergen and a compound of the formula (I) is advantageously formed by bringing the allergen and compound (I) together in the presence of an inert solvent.

The term "inert solvent" as used herein means a solvent for the compound of formula (I), which will not interfere with or otherwise adversely affect the desired course of the method of the invention. Representative of such solvents are a wide variety of ethers, esters, alcohols, ketones, hydrocarbons (aromatic and aliphatic including fluorocarbons), and silicones in which an aqueous phase does not have an appreciable solubility. The solvents may be used either singly or in admixture. Preferred as the inert solvent are the alcohols such as ethanol.

Those skilled in the art will appreciate that in forming the surfactant complex of formula (II) given above in the presence of an alcohol, the allergen may be denatured and thereby rendered biologically inactive. In fact, in the presence of an alcohol denaturization does occur and the desired surfactant complex of allergen and compound (I) will precipitate from the alcoholic mixture as denaturization occurs. The desired precipitate of the complex (II) is conveniently then separated from the alcoholic mixture by filtration and dissolved in an aqueous solution to re-nature the allergen and re-activate its biological activity. The re-natured allergen complex of formula (II) may then be adsorbed on the surface of the carrier particles as described above.

In the next step of the method of the invention, an extra-corporeal specimen of blood serum is obtained from the individual suspected of hosting the reagin or reagins. The specimen may then be mixed with a similar volume of the aqueous dispersion of carrier particles bearing the allergen material and the resulting mixture observed for agglutination of the particles.

To understand further the method of the invention, reference may be now made to the accompanying drawing. The FIGURE is a plan view of a test card showing the results of a reagin identification test carried out according to the method of the invention. The test card, as initially provided may be a smooth, well calendered paper or cardboard with a water-wettable, water-impermeable surface. The test card preferably has a white color to contrast with the charcoal/allergen particles employed in the test method. Indicia are provided on the card surface to identify the particular test, i.e.; a ragweed allergy test in this instance. Space is provided for a date and patient identification. Four test spots or sites are outlined (tear-shaped sites) and identified by indicia as to the test being performed. As shown in the FIGURE, two sites are provided for testing patient sera, one site for a positive control and one site for a negative control. It will be appreciated that the particular arrangement or system of the test card shown in the FIGURE is for exemplification and is not limiting.

On the test card of the FIGURE, from 0.01 to 0.05 ml of patient sera was deposited on each of the test sites identified as "patient sera". To the test site labelled "positive control", 0.01 to 0.05 ml of sera from a human known to be allergic to ragweed is deposited and to the site labelled "negative control", 0.01 to 0.05 ml of human sera known to be free of ragweed reagin is deposited. To each site there is then deposited 0.01 to 0.05 ml of an aqueous suspension of activated charcoal/allergen particles as described above (in this case, particles containing 1.0 to 50.0 mg. of ragweed allergen per ml of water or appropriate buffer. The test card is then placed on a laboratory shaking machine and shaken at 120 gyrations per minute for from 4 to 15 minutes. During this period the mixtures on the test sites are observed. Clumping or agglutination of the suspended particles as shown in the two "patient sera" zones and in the site of the "positive control" are evidence of an allergen-reagin reaction and the absence of clumping or agglutination as shown in the "negative control" site is evidence of a non-reaction of allergen-reagin. In the example of the FIGURE, one may conclude that the patient is allergic to ragweed, since the ragweed reagin was detected in his blood sera. If no agglutination had occurred at the test sites identified for patient sera, one could conclude that the reagin was absent from that patient's sera.

Although the above-described test procedure may be carried out at room temperatures, it is preferred to incubate the reactants during shaking at a temperature of circa 25° C. to 37° C. in a humid atmosphere.

In a preferred embodiment method of the invention, the reagin is first extracted from the blood serum undergoing testing and the extract, a concentrated form of the reagin is used to improve sensitivity of the agglutination reaction. The reagin is advantageously extracted from the blood serum by allowing it to form a complex with anti-IgE reagent previously adsorbed on a solid surface, i.e.; a solid carrier particle as described above. The anti-IgE is advantageously adsorbed on the carrier particles following the same general procedures described above for adsorbing reagin on solid carrier particles.

The following examples describe the manner and process of making and using the invention and set forth the best mode contemplated by the inventors of carrying out the invention but are not to be construed as limiting. All parts given are by weight unless otherwise indicated. In the test results, the relative strength of the allergen-reagin reaction is shown, i.e.; +1, +2, +3 or +4. This is an arbitrary ranking of reaction intensity. The relative strengths are assigned as follows:

Negative—Homogeneous dispersion of particles in the buffer solution. (With charcoal, a negative test is seen as a smooth, homogeneous gray suspension with no obvious particles because the individual particles are microscopic.)

+1 Same as the negative except obvious, macroscopic particles are evident. (With charcoal, these are seen as obvious black aggregates in a gray suspension.)

+2 Same as a +1 but more particles present.

+3 The suspension is now seen almost totally as macroscopic particles. Very few of the microscopic particles are evident.

+4 Virtually all of the microscopic particles have aggregated to form larger, macroscopic particles. These are present in a buffer system that now appears almost totally clear. (With charcoal, this is apparent as dense black particles in a clear solution.)

EXAMPLE 1

Run No. 1

Part A. A solution is prepared consisting of 0.21 percent lecithin and 0.18 percent cholesterol in absolute ethanol. The solution is divided into a plurality of separate vessels, each containing 0.9 ml of the solution. To each vessel there is then added 0.1 ml of a solution of a specific allergen (concentration of allergen ranging from 1.0 to 50.0 mg/ml). The resulting mixture is incubated at room temperature (circa 26° C.) for about 30 minutes. The incubate is then centrifuged and the supernatent decanted. To the residue there is added with stirring 1.0 ml of activated charcoal (average particle size <2.0 μm) suspended in a phosphate buffer (0.01 percent by weight suspension). The resulting suspension is centrifuged and the solids separated and re-suspended in phosphate buffer. The re-suspension is stable for at least a year when stored at a temperature of about 4° C.

Part B. A water-impermeable test card surface is provided and 0.03 ml of the re-suspension for each allergen described above is deposited in a zone of the test card. To the zones there is then added 0.03 ml of blood serum taken from an allergen sensitized human (patient JM). The mixture of serum and allergen suspension is rotated on the card zone for 4 to 12 minutes and the zones observed for any agglutination of charcoal particles.

The allergen employed and the observed agglutination is shown in TABLE 1, below.

Similarly, for control purposes, the above-described procedure is repeated but the allergen is omitted or replaced with gelatin as a control. The results are also shown in TABLE 1 as a negative control.

Run No. 2

The entire procedure described above for Run No. 1 is repeated twice, in a series A and a series B except that in series B the aliquot of blood serum is pre-treated to destroy IgE activity by incubating the serum at a temperature of 56° C. for a period of 30 minutes. The test results are shown in TABLE 1, below.

For comparative purposes, the individual JM is "skin tested" for his sensitivity to allergens by the conventional clinical skin-testing procedure using the same allergens used in the runs 1 and 2 described above. The test reults are also shown in TABLE 1, below.

TABLE 1

| | Patient JM | | | | |
| | | | | Skin Tests | |
| | Run | Run No. 2 | | 10 | 20 |
| Allergen | No. 1 | A | B | Mins | Mins |
| --- | --- | --- | --- | --- | --- |
| 1. Rough Pigweed | — | — | — | +2 | +2 |
| 2. False Ragweed | — | — | — | +2 | +2 |
| 3. Lamb's Quarters | +1 | +2 | — | +2 | +2 |
| 4. G & S Ragweed | ± | +1 | — | +1 | +2 |
| 5. Bermuda Grass | +3 | +1 | +1 | +2 | +2 |
| 6. Russian Thistle | +2 | +1 | +1 | +3 | +2 |
| 7. Sagebrush | +2 | +1 | — | +2 | +3 |
| 8. Johnson Grass | +1 | — | — | +2 | +1 |
| 9. Careless Weed | ± | +1 | — | +2 | +2 |
| 10. Cocklebur | +1 | — | — | +2 | +1 |
| 11. Spiny Pigweed | — | +1 | = | ND | ND |
| 12. Western Pigweed | ± | — | — | +2 | +2 |
| 13. Pecan Tree | — | +1 | — | +2 | +2 |
| 14. *Helminthosporium satium* | | | | | |

TABLE 1-continued

Patient JM

| Allergen | Run No. 1 | Run No. 2 A | Run No. 2 B | Skin Tests 10 Mins | Skin Tests 20 Mins |
|---|---|---|---|---|---|
| 15. Elm Tree Mix | — | — | — | +1 | +1 |
| 16. Western Cottonwood | +2 | — | — | +2 | +3 |
| 17. Sycamore | ± | +1 | — | +1 | +1 |
| 18. Mesquite | ± | +1 | — | +1 | +1 |
| 19. *Hormodendron hordei* | — | — | — | ND | ND |
| 20. House Dust | — | — | — | +2 | +1 |
| 21. *Alternaria tenius* | — | — | — | +1 | +1 |
| 22. Mountain Cedar | +3 | +3 | +1 | +3 | +3 |
| 23. Oak Mix | +1 | +1 | — | +1 | +1 |
| 24. *Penicillium notatium* | — | — | — | +1 | +2 |
| 25. *Aspergillus fumigatus* | — | — | — | — | — |
| 26. Pigweed | ND | +3 | +1 | +2 | +2 |
| 27. Timothy | ND | +1 | — | +2 | +2 |
| 28. Kochia | ND | +1 | — | +4 | +3 |
| 29. Hackberry | ND | +1 | — | +2 | +2 |
| 30. Juniper | ND | — | — | +2 | +2 |
| 31. Black Willow | ND | +1 | ND | +1 | +2 |
| 32. Pecan | ND | +2 | ND | +1 | +2 |
| 33. Grain Mill Dust | ND | — | — | +2 | +2 |
| 34. Tobacco | ND | — | — | +2 | +3 |
| 35. Feathers | ND | +1 | — | +2 | +2 |
| 36. Horse | ND | — | ND | +3 | +3 |
| 37. Dog | Nd | — | ND | +3 | +3 |
| 38. Cat | ND | — | ND | ND | ND |
| 39. Stinging Insect Mix | ND | — | ND | ND | ND |
| 40. Negative Control | — | — | ND | +1 | +1 |
| 41. Charcoal Resuspending Fluid Only | ND | — | ND | ND | ND |

A = Non-heated serum
B = Heated serum
ND = Not Done

EXAMPLE 2

The procedure of Example 1, supra., is repeated except that the patient JM is replaced with a different human patient SH. The results are shown in Table II, below.

TABLE II

| Allergen | Run No. 1 | Run No. 2 A | Run No. 2 B | Skin Tests 10 min. | Skin Tests 20 min. |
|---|---|---|---|---|---|
| 1. Rough Pigweed | +1 | +1 | +1 | +1 | +1 |
| 2. False Ragweed | +1 | — | — | +1 | +1 |
| 3. Lamb's Quarters | — | — | — | +1 | +1 |
| 4. G & S Ragweed | — | — | — | +1 | +1 |
| 5. Bermuda Grass | +1 | +1 | +1 | +1 | +1 |
| 6. Russian Thistle | +2 | +1 | +1 | +2 | +2 |
| 7. Sagebrush | +1 | — | — | +2 | +2 |
| 8. Johnson Grass | +1 | +1 | — | +2 | +2 |
| 9. Careless Weed | — | — | — | +1 | +1 |
| 10. Cocklebur | — | — | — | +2 | +1 |
| 11. Spiny Pigweed | +1 | +1 | +1 | +1 | +1 |
| 12. Western Pigweed | W | — | — | +1 | +1 |
| 13. Pecan Tree | W | +1 | — | +1 | +1 |
| 14. *Helminthosporium satium* | — | +1 | — | ND | ND |
| 15. Elm Tree Mix | — | — | — | +1 | +1 |
| 16. Western Cottonwood | — | — | — | +2 | +2 |
| 17. Sycamore | — | +1 | — | +2 | +2 |
| 18. Mesquite | — | — | — | +1 | +1 |
| 19. *Hormodendron hordei* | +1 | +2 | +1 | +2 | +2 |
| 20. House Dust | — | — | — | +2 | +2 |
| 21. *Alternaria tenius* | — | — | — | +1 | +1 |
| 22. Mountain Cedar | +3 | +3 | +3 | +2 | +2 |
| 23. Oak Mix | +1 | — | — | +2 | +1 |
| 24. *Penicillium notatium* | W | — | — | +2 | +2 |
| 25. *Aspergillus fumigatus* | +1 | — | — | +2 | +2 |
| 26. Pigweed | +1 | +1 | +1 | +1 | +1 |
| 27. Timothy | — | — | — | +1 | +1 |
| 28. Kochia | — | — | — | +2 | +2 |
| 29. Hackberry | W | — | — | +2 | +2 |
| 30. Juniper | +1 | — | — | +2 | +2 |
| 31. Black Willow | — | — | — | +1 | +1 |
| 32. Pecan | +1 | +2 | +1 | +1 | +1 |
| 33. Grain Mill Dust | — | — | — | +1 | +1 |
| 34. Tobacco | — | — | — | +2 | +2 |
| 35. Feathers | — | — | ND | +1 | +1 |
| 36. Horse | W | — | ND | +2 | +2 |
| 37. Dog | +1 | — | ND | +2 | +2 |
| 38. Cat | +1 | — | ND | ND | ND |
| 39. Stinging Insect Mix | — | — | ND | ND | ND |
| 40. Negative Control | — | — | — | +1 | +1 |
| 41. Charcoal Resuspending Fluid Only | ND | — | ND | ND | ND |

W = Weak
ND = Not Done
A = non-heated serum
B = heated serum

Example 3

The general procedure of Example 1, Run No. 1 is repeated 5 times, each time employing blood serum from a different human patient (identified as VF, CAR, CAG, LWI and LAN, respectively). The individuals are also skin tested for their sensitivity to allergens. The test results are shown in Table III, below.

TABLE III

| Allergen | (VF) Charcoal | (VF) Skin Test | (CAR) Charcoal | (CAR) Skin Test | (CAG) Charcoal | (CAG) Skin Test | (LWI) Charcoal | (LWI) Skin Test | (LAN) Charcoal | (LAN) Skin Test |
|---|---|---|---|---|---|---|---|---|---|---|
| Tree Mix | +4 | +3 | +4 | +3 | +3 | +2 | +2 | +1 | +2 | +1 |
| Grass Mix | +3 | +2 | +4 | +5 | +4 | +1 | +3 | +4 | +3 | +1 |
| Thistle | +1 | +2 | +1 | +2 | +2 | +1 | +1 | +2 | +1 | +3 |
| Spiney Pigweed | +4 | +1 | +4 | +1 | +4 | +1 | +3 | +1 | +2 | +3 |
| Ragweed/False R. | +1 | +1 | +2 | +4 | +1 | +2 | — | +3 | +2 | +3 |
| SWM/BSA[1] | +3 | +3 | +4 | +3 | +4 | +2 | +4 | +1 | +4 | +2 |
| Mesquite | +2 | +2 | +3 | +3 | +2 | +1 | +1 | +1 | +2 | +1 |
| Mtn. Cedar | +3 | +2 | +4 | +3 | +3 | +3 | +3 | 1 | +3 | +3 |
| MAD/C[2] | +1 | +1 | +2 | +k | +2 | +2 | +1 | +1 | +2 | +3 |
| Dust | +3 | +2 | +4 | +3 | +3 | +1 | +3 | +2 | +2 | +1 |
| Common Mold | +2 | +1 | +2 | +1 | +1 | +2 | +1 | +1 | +1 | +4 |
| Area Mold | +3 | +1 | +4 | +1 | +3 | +2 | +2 | ND | +2 | +3 |
| Pecan | +4 | +5 | +3 | +1 | +2 | +3 | +1 | +1 | +1 | +1 |
| RWM[3] | +4 | ND | +4 | +2 | +2 | +1 | +3 | +2 | +3 | +2 |
| 2% BSA[4] | — | ND | — | ND | — | ND | — | ND | — | ND |

TABLE III-continued

| | (VF) | | (CAR) | | (CAG) | | (LWI) | | (LAN) | |
|---|---|---|---|---|---|---|---|---|---|---|
| Allergen | Charcoal | Skin Test | Charcoal | Skin Test | Charcoal | Skin Test | Charcoal | Skin Test | Charcoal | Skin Test |
| Correlation | 100% | | 100% | | 100% | | 92.3% | | 100% | |

[1]Mixture of Kochia, Plantain, Cocklebur, Marsh elder, Sagebrush/Broomweed, Sheep sorrel, Atriplex.
[2]Mixed animal danders/cat.
[3]Russian Thistle, Spiney Pigweed, Ragweed, Franseria.
[4]Negative Control - Bovine serum albumin.

EXAMPLE 4

(A) A solution is prepared of 0.21 percent lecithin and 0.18 percent cholesterol in absolute ethanol. The solution is divided into a plurality of separate vessels, each containing 0.9 ml of the solution. To each vessel there is then added 0.01 ml of antiserum to human IgE (ε-chain specific; produced in either goats or rabbits). The resulting mixture is incubated at room temperature (circa 26° C.) for about 30 minutes and the incubate is then centrifuged (1200 Xg) for 15 minutes. The supernatent is decanted and the residue is added with stirring to 1.0 ml of a suspension of 0.01% activated charcoal (average particle size $<2.0\mu m$) in phosphate buffer (pH=7.2). The resulting suspension is centrifuged again and the solids separated and re-suspended in phosphate buffer (pH=7.2).

(B) To 0.1 ml of the suspension prepared in step (A) above there is added 0.1 ml of human blood serum taken from a given individual sensitive to an allergen. The mixture is incubated at a temperature of 37° C. with gentle shaking for a period of about 45 minutes. At the end of this period, the incubate is centrifuged (1200 Xg) and the residue separated to obtain a complex of charcoal/anti-IgE/patient IgE. The complex is suspended in 0.1 ml of phosphate buffer (pH=7.2).

EXAMPLE 5

Part(A) The procedure of Example 1, Run No. 1 Part (A) is repeated, but the specific allergen as used therein is replaced with an equal volume of anti-IgE to obtain a suspension of activated charcoal particles having adsorbed therein anti-IgE.

To 0.1 ml of blood serum obtained from an allergen sensitized human, there is added with mixing 0.1 ml of the suspension of activated charcoal/anti-IgE. With continued mixing, the resulting mixture is incubated at a temperature of 37° C. for a period of 15 minutes. At the end of the incubation period, the mixture is filtered to remove a complex of activated charcoal/anti-IgE-IgE. The complex (filter residue) is re-suspended in 0.1 ml. of phosphate buffer.

Part(B) A plurality of water-impermeable test card surfaces are provided and 0.01 ml. of the activated charcoal/anti-IgE/IgE complex suspension described above is deposited in a zone of the test card. To each zone there is then added 0.01 ml of one of an allergen suspension of Example 1, Run No. 1, Part A, supra. The mixtures of complex and allergens is rotated on the card for 4 to 12 minutes and the zones observed for agglutination of charcoal particles. The degree of agglutination for each different allergen containing zone is shown below in Table IV. For control purposes, the procedure of this Example 5 is repeated, except that the blood serum used is first heated to a temperature of 56° C. for 30 minutes to destroy IgE activity. No agglutination was observed with the control run. As a means of comparison, skin testing for allergen sensitivity is carried out on the individual source of the blood serum. The response to the skin testing is also shown in the Table IV below, showing the strength of the allergic reaction.

EXAMPLE 6

To an appropriate vessel charged with a 10 percent suspension of killed *S. aureus* in buffer (pH 7.2) there is added 1 ml of anti-IgE. The resulting mixture is incubated for 2 hours on a rocker, at a temperature of circa 26° C. At the end of this period, the mixture is centrifuged and the pellet washed and re-suspended in buffer (pH 7.2) to obtain particles of *S. aureus* protein A particles having adsorbed therein anti-IgE.

The procedure of Example 5, supra. is repeated except that the activated charcoal/anti-IgE particle suspension as used therein is replaced with the *S. aureus* protein A particle suspension obtained above. The results of the test procedure are given in the Table IV below, indicating the strength of the allergen-reagin reaction.

TABLE IV

| Example No. | Bermuda | Reagin Tested For Russian Thistle | Orchard Grass |
|---|---|---|---|
| 5 | +3 | +1 | +3 |
| 6 | +3 | +3 | +3 |
| Skin tests (control) | +2 | +3 | +2 |

EXAMPLE 7

Determination of Total IgE

The procedure of Example 5, supra., is repeated, except that anti-IgE as used in Part (A) was replaced with an equal proportion of sheep anti-IgE purified by removal of IgG. In Part (B), 50 μl of patient serum (patient TR, an allergen-sensitive human patient) was mixed with 10 μl of the sheep anti-IgE-charcoal complex from Part (A) in each of the test card test zones and the card was rotated for 4, 8, 12 and 16 minutes, respectively, while observed for agglutination. The observed results are shown in the Table V, below.

The procedure of this example was also repeated a number of times, replacing the blood serum of the patient TR with IgE free equine serum and with a variety of known, IgE containing reference standards (Seward, Kallestad). The results are also given in the Table V, below. The level of total IgE in each serum was determined by the PRIST technique, and the determinations are also given in Table V.

TABLE V

| Sample | 4 Min. | 8 Min. | 12 Min. | 16 Min. | PRIST IgE Level* |
|---|---|---|---|---|---|
| Patient TR | +2 | +3 | +4 | +4 | 660 units/ml |
| Patient TR (with IgE removed) | — | ± | +1 | +1 | <50 units/ml |
| Seward IgE | +2 | +3 | +3 | +3 | 250 units/ml |
| Kallestad Reference I | +2 | +2 | +2 | +3 | 13 units/ml |
| Kallestad Reference II | +2 | +2 | +2 | +2 | 37 units/ml |
| Kallestad Reference III | +2 | +3 | +3 | +3 | 110 units/ml |
| IgE free equine serum (1:20) | — | — | — | — | — |

*As measured by Pharmacia Diagnostic's PRIST Total IgE Assay.

To evaluate the sensitivity of the method of the invention to determine total IgE, a series of dilutions of the serums (TR serum, Seward and Kallestad standard references) were made up in 1:20 IgE free equine serum in phosphate buffered saline (pH 7.2). The diluted serums were assayed for IgE by the procedure of Example 7, supra. The dilutions used and the assay results are shown in TABLE VI, below.

TABLE VI

| Sample | PRIST Measured IgE (units/ml) | 1:1 Time (min.) | | | | 1:6 Time (Min.) | | | | 1:36 (Time min.) | | | | 1:216 (Time min.) | | | | IgE Detec (units/ml) |
|---|---|---|---|---|---|---|---|---|---|---|---|---|---|---|---|---|---|---|
| | | 4 | 8 | 12 | 16 | 4 | 8 | 12 | 16 | 4 | 8 | 12 | 16 | 4 | 8 | 12 | 16 | |
| Patient TR | 600 | +4 | +4 | +4 | +4 | +4 | +4 | +4 | +4 | +3 | +4 | 4 | 4 | — | 1 | 2 | 3 | 3 |
| Seward | 2000 | — | — | — | — | — | 2 | 2 | 2 | 2 | 2 | 2 | 2 | 2 | 2 | 2 | 2 | 9* |
| Kallestad Reference I | 14 | 1 | 1 | 2 | 2 | — | ± | 1 | 2 | — | — | — | — | — | — | — | — | 2-3 |
| Kallestad Reference II | 82 | 1 | 1 | 2 | 3 | — | ± | 1 | 2 | — | — | — | — | — | — | — | — | 14 |
| Kallestad Reference III | 244 | 1 | 1 | 2 | 2 | 1 | 2 | 2 | 3 | — | — | 1 | 1 | — | — | — | — | 7 |
| PRIST Standard | 100 | — | 2 | 3 | 3 | — | — | 2 | 2 | — | — | 1 | 2 | — | — | ± | ± | 3 |

*Actually carried to 1:1296 and got +2, +2, +2 and +2 for detection of 1.5 units/ml.

The Table VI demonstrates that the sensitivity of the assay of the invention appears to be about 2 units/ml IgE. Dilution of an unknown sample to loss of agglutination can be used as a semiquantitative determination of total IgE.

What is claimed:

1. A method of determining the presence of absence of a given reagin in the blood serum of a vertebrate sensitized by a polar allergen corresponding to said reagin, which comprises;
   A. providing an in-vitro specimen of the blood serum suspected of containing the reagin;
   B. providing an aqueous dispersion of solid, non-polar hydrophobic carrier particles having adsorbed thereon a first complex of said polar allergen and a phospholipid compound and a second complex of said allergen and a non-phospholipid compound, said phospholipid and said non-phospholipid compounds both being a compound of the formula: X—Y wherein X represents a hydrophilic, polar moiety and y represents a hydrophobic, non-polar, moiety, said first and second complexes having the formula:

Ⓐ X—Y wherein X and Y have the meanings ascribed to them above and Ⓐ is the polar allergen molecule, and wherein X and Y are chemically bound together and the X—Y compound is complexed with the allergen such that the Y moiety is oriented away from the polar allergen molecule;
   C. admixing the blood serum provided with the aqueous dispersion; and
   D. observing the mixture obtained for an agglutination reaction;
   wherein a positive reaction is indicative of the presence of said reagin and a negative reaction is indicative of the absence of said reagin.

2. The method of claim 1 wherein said vertebrate is a human.

3. The method of claim 1 wherein said carrier particles are activated charcoal.

4. The method of claim 1 wherein the admixture of serum and aqueous dispersion is incubated at a temperature of circa 25° C. to 37° C.

5. A method of determining the presence or absence of a reagin in the blood serum of a verebrate sensitized by a polar allergen counterpart of said reagin, which comprises;
   A. providing an extra-corporeal specimen of the blood serum upon which the determination is to be made;
   B. extracting any reagin present in the blood serum, from the blood serum by complexing it with anti-IgE adsorbed on a solid particle;
   C. providing an aqueous dispersion of solid non-polar hydrophobic carrier particles having adsorbed thereon an allergen corresponding to said allergen counterpart, said allergen being in the form of a complex of the formula:

Ⓐ X—Y wherein X represents a hydrophilic, polar moiety, Y represents a hydrophobic non-polar moiety and Ⓐ is the polar allergen molecule, and where X and Y are chemically bound together and the X—Y compound is complexed with the allergen such that the Y moiety is oriented away from the polar allergen molecule;
   D. admixing the extract complex with the aqueous dispersion; and
   E. observing the admixture for an agglutination reaction;

wherein a positive agglutination reaction is indicative of the presence of the reagin and the absence of an agglutination reaction is indicative of the absence of the reagin.

6. The method of claim 5 wherein the anti-IgE is adsorbed on activated charcoal particles.

7. The method of claim 5, wherein the particles are activated charcoal.

8. The method of claim 7 wherein the anti-IgE is adsorbed on activated charcoal particles.

* * * * *